United States Patent
Vu et al.

(10) Patent No.: US 9,510,920 B2
(45) Date of Patent: Dec. 6, 2016

(54) METHOD FOR PRODUCING AT LEAST ONE PATIENT-SPECIFIC MODULARLY COMPOSED BRACKET BODY AND CORRESPONDING BRACKET

(75) Inventors: Hoang Viet-Ha Julius Vu, Unna (DE); Dirk Wiechmann, Bad Essen (DE)

(73) Assignee: DW Lingual Systems GmbH, Bad Essen (DE)

( * ) Notice: Subject to any disclaimer, the term of this patent is extended or adjusted under 35 U.S.C. 154(b) by 0 days.

(21) Appl. No.: 13/984,465

(22) PCT Filed: Feb. 8, 2012

(86) PCT No.: PCT/EP2012/052148
§ 371 (c)(1),
(2), (4) Date: Aug. 8, 2013

(87) PCT Pub. No.: WO2012/107501
PCT Pub. Date: Aug. 16, 2012

(65) Prior Publication Data
US 2013/0323666 A1    Dec. 5, 2013

(30) Foreign Application Priority Data
Feb. 9, 2011    (DE) .................. 10 2011 003 892

(51) Int. Cl.
*A61C 7/14*    (2006.01)
*A61C 7/00*    (2006.01)
*A61C 13/00*    (2006.01)

(52) U.S. Cl.
CPC .............. *A61C 7/14* (2013.01); *A61C 7/002* (2013.01); *A61C 13/0004* (2013.01); *Y10T 29/49568* (2015.01)

(58) Field of Classification Search
CPC .......... A61C 7/00; A61C 7/002; A61C 7/02; A61C 7/12–7/16

USPC ........................................................ 433/2–24
See application file for complete search history.

(56) References Cited

U.S. PATENT DOCUMENTS 2,701,913 A * 2/1955 Lane ................................ 433/16
4,165,561 A * 8/1979 Miller et al. ...................... 433/9
(Continued)

FOREIGN PATENT DOCUMENTS

EP    0 502 227    11/1996
EP    1 844 730    10/2007
(Continued)

OTHER PUBLICATIONS

International Preliminary Report on Patentability and Written Opinion, Aug. 22, 2013, Hoang Viet-Ha Julius Vu.

*Primary Examiner* — Edward Moran
(74) *Attorney, Agent, or Firm* — Greer, Burns & Crain, Ltd.; Steven P. Fallon

(57) ABSTRACT

A method for producing a patient-specific modular bracket having a pad and a bracket body. A bracket body library of bracket bodies includes bodies that are formed from a raw bracket body having a spacer section. A first parameter is established for cutting through the spacer section from a slot of the bracket body to set a height of the bracket body. A second parameter is established for cutting through the spacer section at an angle to a mesio-distal axis of the bracket body to set a torque value of the bracket body. A third parameter is established for cutting through the spacer section at an angle to an occlusal-gingival axis to set a rotation value of the bracket body. The spacer section is cut through according to the first, second and third parameters. Patient specific set-ups are then created by selecting and attaching pads from a raw pad library.

17 Claims, 14 Drawing Sheets

(56) References Cited

U.S. PATENT DOCUMENTS

| | | |
|---|---|---|
| 4,369,033 A | 1/1983 | Webb et al. |
| 5,454,717 A | 10/1995 | Adreiko et al. |
| 5,971,754 A * | 10/1999 | Sondhi et al. ............ 433/24 |
| 2002/0010568 A1 | 1/2002 | Rubbert et al. |
| 2010/0324715 A1 * | 12/2010 | Yang et al. ............ 700/98 |

FOREIGN PATENT DOCUMENTS

| | | |
|---|---|---|
| EP | 1 941 842 | 7/2008 |
| EP | 1 474 064 | 11/2008 |

* cited by examiner

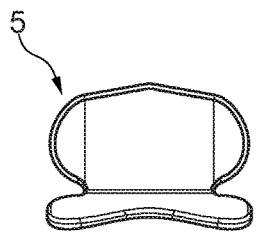
Fig. 3F
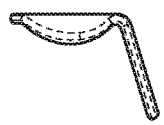 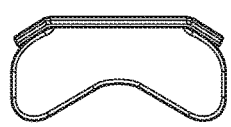 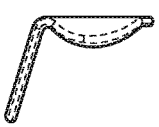 
Fig. 3B     Fig. 3C     Fig. 3D     Fig. 3E
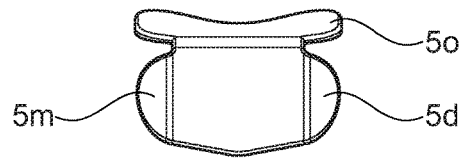
Fig. 3A
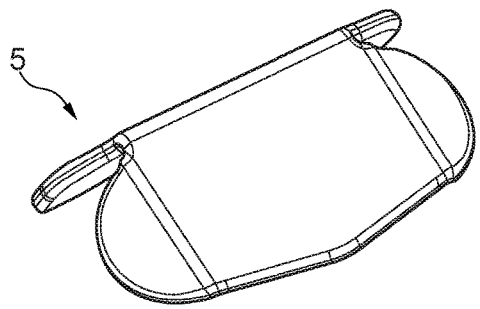
Fig. 3G

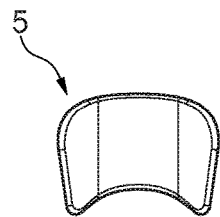
Fig. 4F
   
Fig. 4B   Fig. 4C   Fig. 4D   Fig. 4E
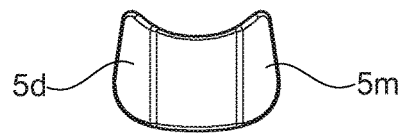
Fig. 4A
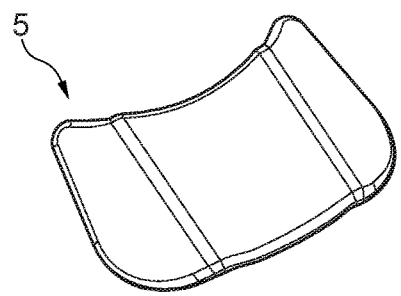
Fig. 4G

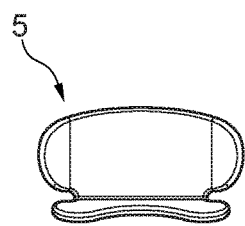
Fig. 5F
 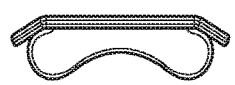  
Fig. 5B     Fig. 5C     Fig. 5D     Fig. 5E
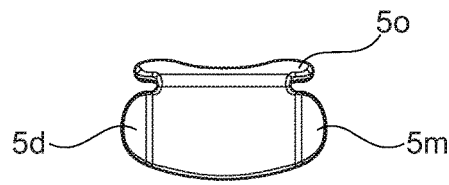
Fig. 5A
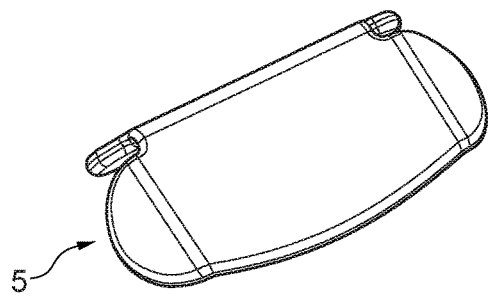
Fig. 5G

ROTATION

TORQUE

ROTATION

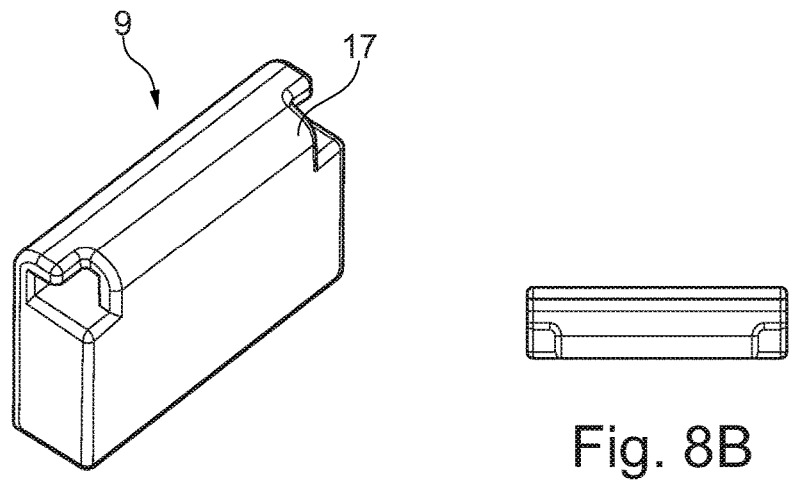
Fig. 8A
Fig. 8B
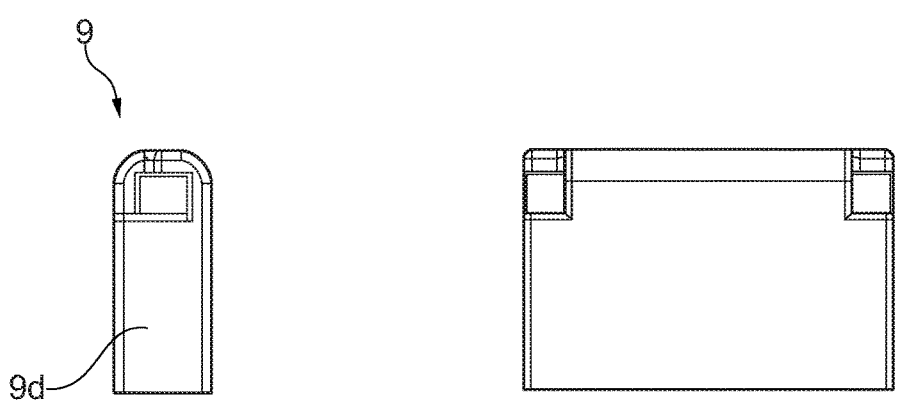
Fig. 8C
Fig. 8D

METHOD FOR PRODUCING AT LEAST ONE PATIENT-SPECIFIC MODULARLY COMPOSED BRACKET BODY AND CORRESPONDING BRACKET

PRIORITY CLAIM AND REFERENCE TO RELATED APPLICATION

The application claims priority under all applicable treaties and statutes from and is a 35 U.S.C. 371 of PCT/EP2012/052148, filed Feb. 8, 2013, which application claimed priority from German Application No. 10 2011 003 892.2, which was filed on Feb. 9, 2011.

The invention concerns a method for producing at least one patient-specific bracket body designed in a modular system and a corresponding bracket.

For the orthodontic treatment of patients having fixed braces, brackets are glued on the teeth of the patient to be treated and connected to one another via an archwire, so that they form an arrangement of brackets with respectively a slot through which an archwire can be run. The brackets present a pad for connection with the tooth and a bracket body, which in particular receives the archwire in a slot.

Standard brackets can be used as brackets, which are normalised according to certain standard values and may hence be used for a certain range of patients. There is also the possibility to have brackets manufactured individually for patients as disclosed for instance in EP1474064B1, EP07111572A1, US20020010568A1 and EP08103240.

While the manufacture of standard brackets does not raise any problems, the production of completely individualised brackets is quite wasteful. In a variation, individual bracket components such as for instance a hook, a wing, a slot for receiving an arch wire and a pad for setting up on a tooth are available in a computer, which are then assembled to build a virtual bracket, wherein this takes place in a virtual set-up of a patient's denture. The virtual bracket so obtained is transferred to a 3D printer to manufacture a real bracket therewith.

The standard brackets have been perceived as detrimental inasmuch as they do not allow for individualisation for a given patient. The wasteful production has been perceived as detrimental with completely individualised brackets.

The object of the present invention is hence to manufacture a patient-specific bracket body in a simple way.

GENERAL DESCRIPTION OF THE INVENTION

This object is satisfied by a method having the characteristics of the claims and a bracket manufactured according to the method.

The process in particular relates to the production of a patient-specific bracket that is designed in a modular system, the bracket having a pad and a bracket body by:
1a) providing a raw pad library having raw pads,
1b) providing at least one bracket body library of raw bracket bodies,
1c) generating a patient-specific model of the dentition (set-up), in particular made of plaster, of the teeth to be treated of an upper jaw and/or of a lower jaw of a patient,
1d) selecting a raw pad from the raw pad library for each of the patient's tooth to be treated,
1e) forming a patient-specific glued surface on each raw pad for producing a pad having a patient-specific surface, in particular by arranging the raw pad at a spacing to the model of the dentition and filling the gap extending over the spacing using filling material and hardening of the filling material,
1f) selecting a bracket body from the bracket body library for each pad for connecting one bracket body each with a pad,
1g) connecting one pad each to the corresponding bracket body for producing a bracket for each tooth of the patient to be treated.

The bracket bodies of the bracket body library are advantageously provided by:
2a) providing a raw bracket body having a spacer section,
2b) establishing a first parameter for cutting through the spacer section, a distance of a resulting cut surface of the spacer section from the slot in order to establish a suitable height of the bracket body,
2c) establishing a second parameter for cutting through the spacer section, a cutting angle to a mesio-distal axis, in order to establish a suitable torque value of the bracket body,
2d) establishing a third parameter for cutting through the spacer section, a cutting angle to an occlusal-gingival axis in order to establish a suitable rotation value of the bracket body,
2e) cutting through the spacer section according to the three established parameters, especially by means of a saw, whereby a bracket body is produced.

The raw pads of the raw pad library are advantageously provided by:
3a) providing a pad material section, which preferably is plane,
3b) providing a punch having at least one punching stamp for punching out at least one raw pad from the pad material section,
3c) punching out of at least one raw pad from the pad material section by means of the punch.

The raw bracket bodies are preferably manufactured by a MIM process or a selective laser melting process.

The pad material section and/or the raw bracket bodies are advantageously generated from a biocompatible metal or a biocompatible alloy, in particular titanium, gold, silver or stainless steel or a cobalt-chrome alloy.

The connection of each pad to its corresponding bracket body preferably is made by glueing or welding.

To produce a bracket, a pad for connection with a bracket body is prepared for every tooth of a patient to be treated.

The generation of a patient-specific glued surface on a raw pad in section 1e) preferably is made by filling of a gap between the raw pad and the corresponding tooth in the set-up using a filling material, especially of plastic, in order to allow for a positive form fit of the glued surface to the clinical tooth of the patient.

At least two parameters, especially the second one and the third one, are each advantageously varied in steps 2b) to 2d) in a selected interval limit with selected interval steps in order to generate the bracket body library, wherein bracket bodies are arranged with their respective differing parameter values.

In step 1a), in the raw pad library preferably raw pads are provided which are pre-assembled to a specific tooth each, e.g. raw pads which are pre-assembled in at least one compression step following the stamping out, especially raw pads pre-assembled to a respective tooth of an upper jaw and/or of a lower jaw.

The pre-assembly preferably comprises an adaptation of the buccal/lingual perimeter of the at least one raw pad in order to adapt the perimeter of the raw pad to a certain tooth size or tooth form.

The pre-assembly preferably includes a bending of selected sections of a raw pad, in particular the bending of mesial and/or distal sections of a raw pad, to build mesial and/or distal wing sections of the raw pad which encompass the corresponding tooth at least by sections.

The pre-assembly preferably includes a bending of an occlusal section of a raw pad, which then rests occlusally on the corresponding tooth.

The pre-assembly preferably includes the formation of lingual/buccal protrusions on at least one raw pad, e.g. to adapt it to a lingual concave/convex structure of a certain tooth.

Advantageously, a manual adaptation of the raw pad selected in step 1d) to its corresponding tooth is made, wherein said adaptation can include an adaptation of the form and/or of the size of the raw pad.

Advantageously, at least two different raw bracket bodies are provided, which each are adapted to a certain tooth, especially eight, i.e. a raw bracket body for each tooth (1st to 8th), and in step 1b) the raw bracket libraries are provided therefrom.

Preferably, the brackets are respectively positioned in a malocclusion model of the patient on the matching tooth to be treated and a transfer tray is then obtained.

The process is further characterized by the selection of a combination of bracket body and pad each from a library of pre-made bracket bodies and pads, respectively, especially including the connection of a bracket body, the spacer section of which has a cut surface arranged according to the three parameters, with the pad, the patient-specific surface of which is formed by a hardened filling material formed by contact with the model of the dentition. The bracket body preferably comprises a cut surface spaced by a spacer section, which is obtained by cutting through, in particular sawing. The spacer section spaces the cut surface apart from the slot of the bracket body and has a length which as a first parameter establishes a suitable height of the bracket body. The cut surface is allocated to the mesio-distal axis as a second parameter in a cutting angle and establishes a suitable torque value of the bracket body. Additionally, the cut surface is allocated to the occlusal-gingival axis as the third parameter in a cutting angle, which establishes a suitable rotation value of the bracket body. The cut surface is hence established by the three parameters. By connection of the cut surface of the spacer section of the bracket body with the pad, which in particular presents a flat surface, preferably a constant material thickness, the arrangement of the bracket body with respect to the pad is established by the three parameters, and hence establishes the arrangement of the slot in the bracket body, adapted for the three parameters on the pad.

DETAILED DESCRIPTION OF THE INVENTION

Additional characteristics, details and advantages of the invention can be seen in the claims and the following description of preferred embodiments as well as using the drawing. The figures are as follows:

FIGS. 3A-3G show several views of a raw pad for the tooth 27,

FIGS. 4A-4G show several views of a raw pad for the tooth 35,

FIGS. 5A-5G show several views of a raw pad for the tooth 37,

Figure 1B:
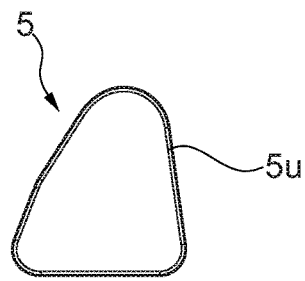
FIGS. 1A-1D show several views of a raw pad for the tooth 21.
Figure 1D:
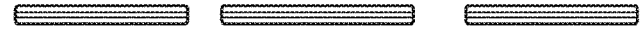
Figure 1A:
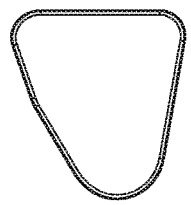
Figure 1C:
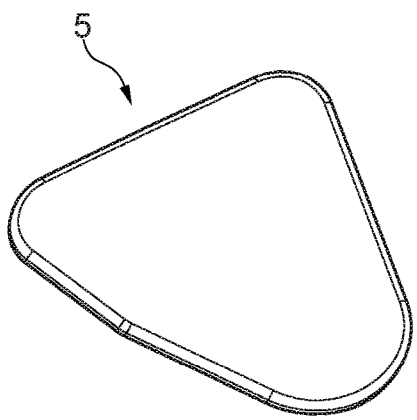
Figure 2B:
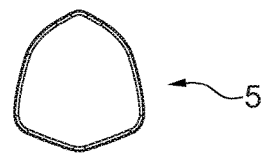
FIGS. 2A-2D show several views of a raw pad for the tooth 23.
Figure 2D:
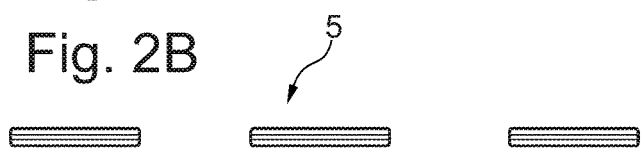
Figure 2A:
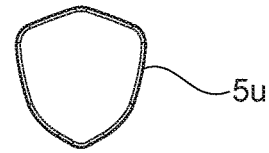
Figure 2C:
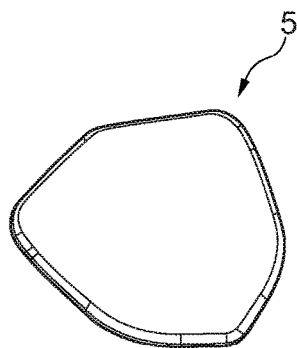
Figure 6A:
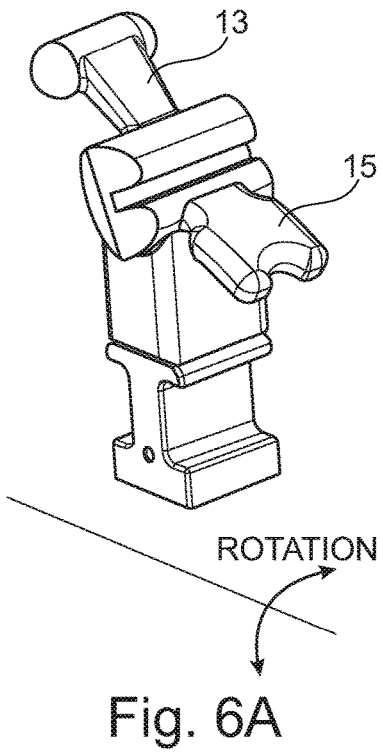
Figure 6B:
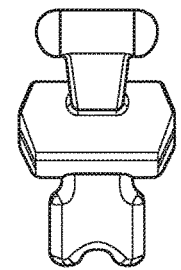
Figure 6C:
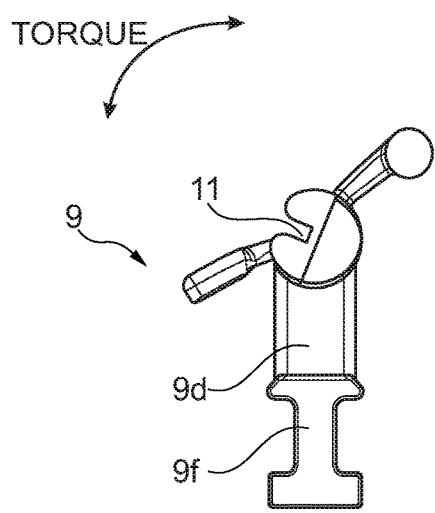
Figure 6D:
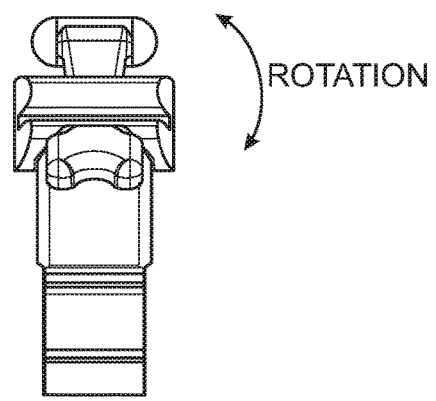
Figure 6E:
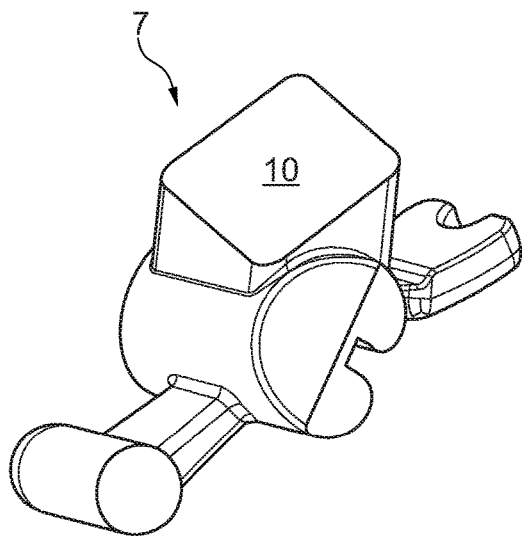
Figure 6F:
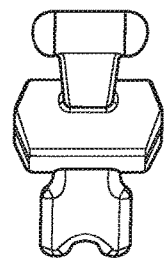
Figure 6H:
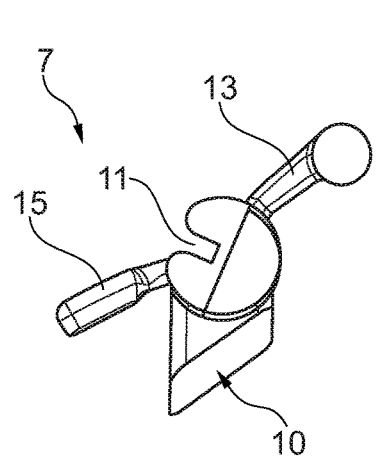
Figure 6G:
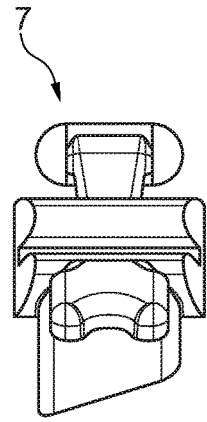
Figure 7A:
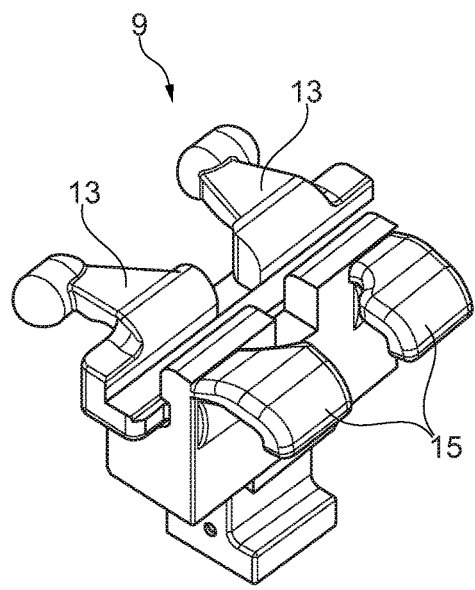
Figure 7B:
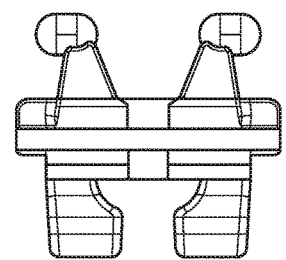
Figure 7C:
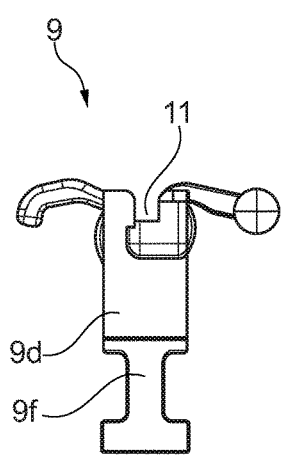
Figure 7D:
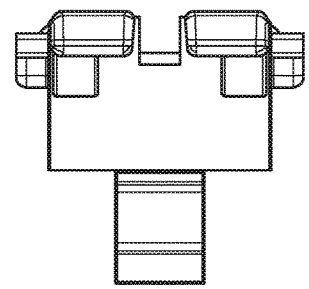
Figure 8E:
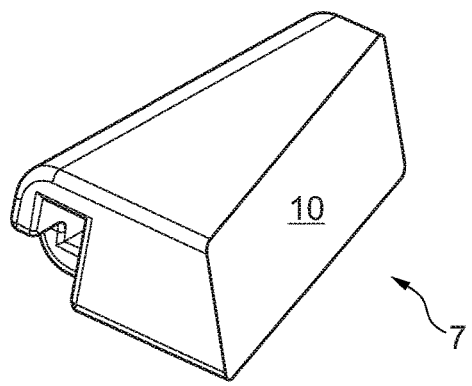
Figure 8F:
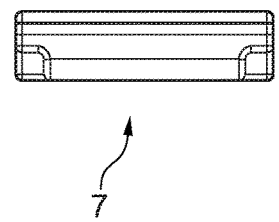
Figure 8G:
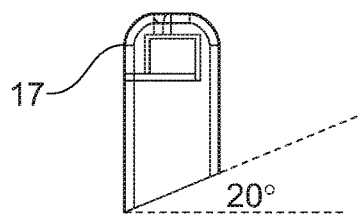
Figure 8H:
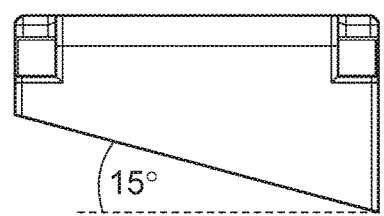
Figure 9:
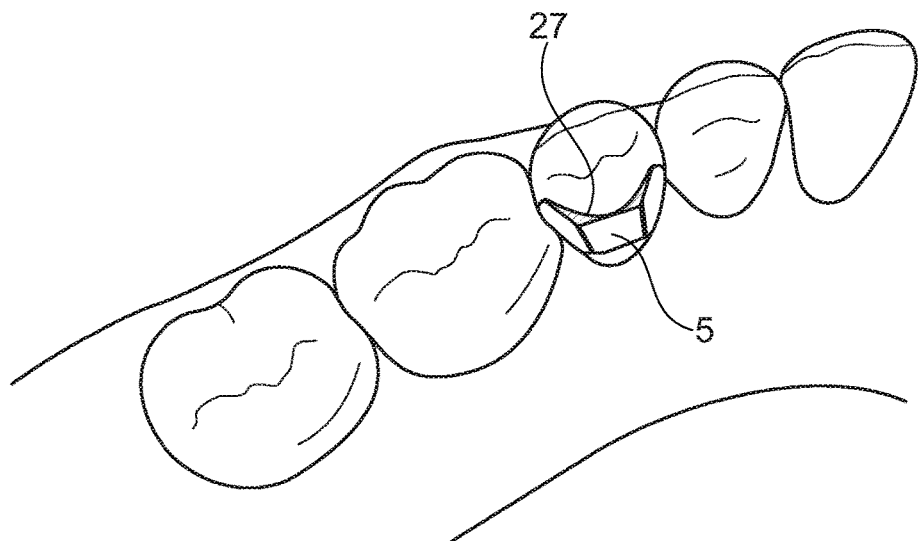
Figures 10A, 10B:
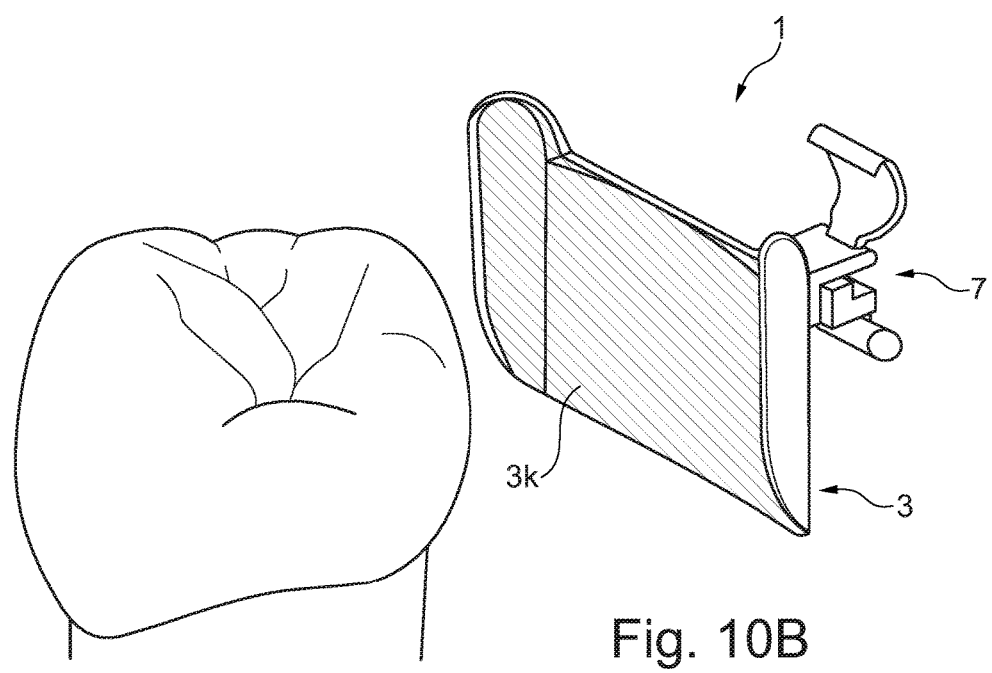
Figure 11:
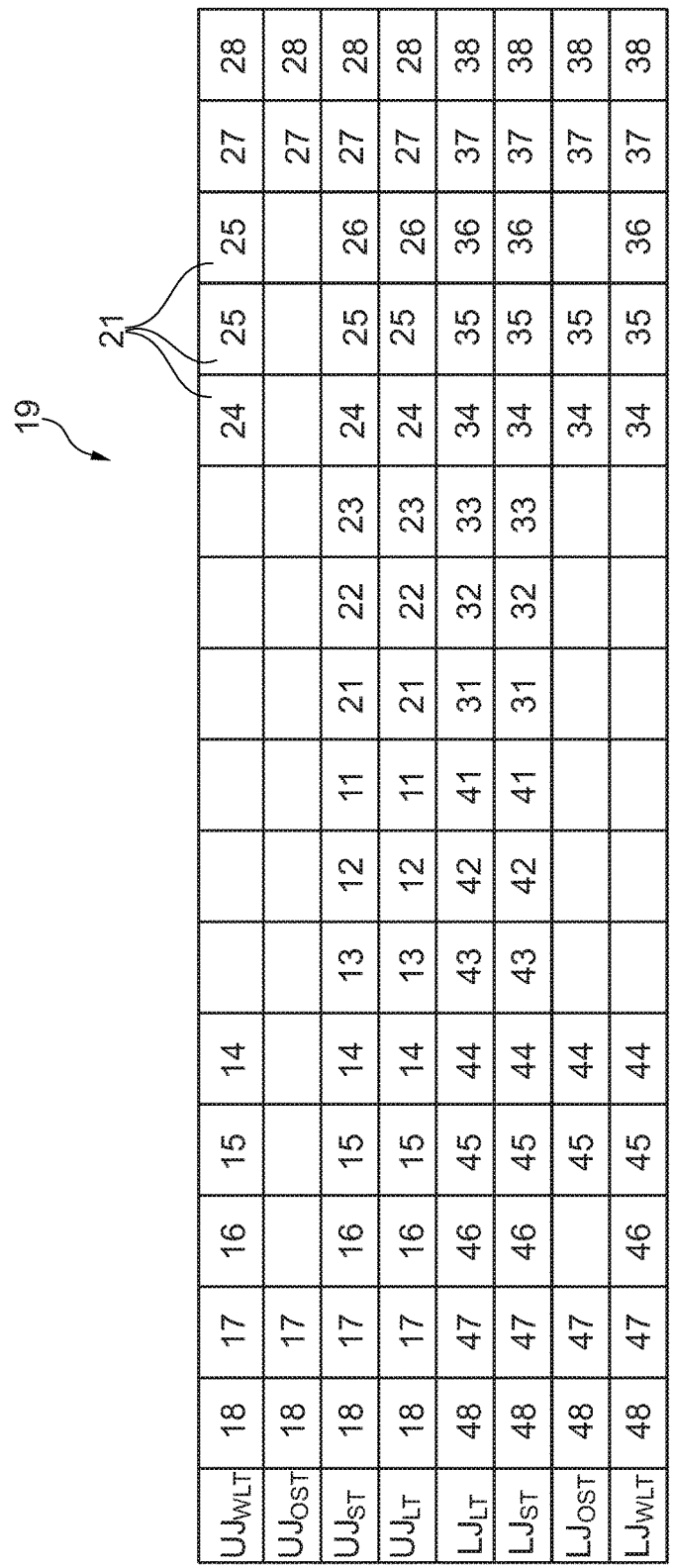
Figure 12:
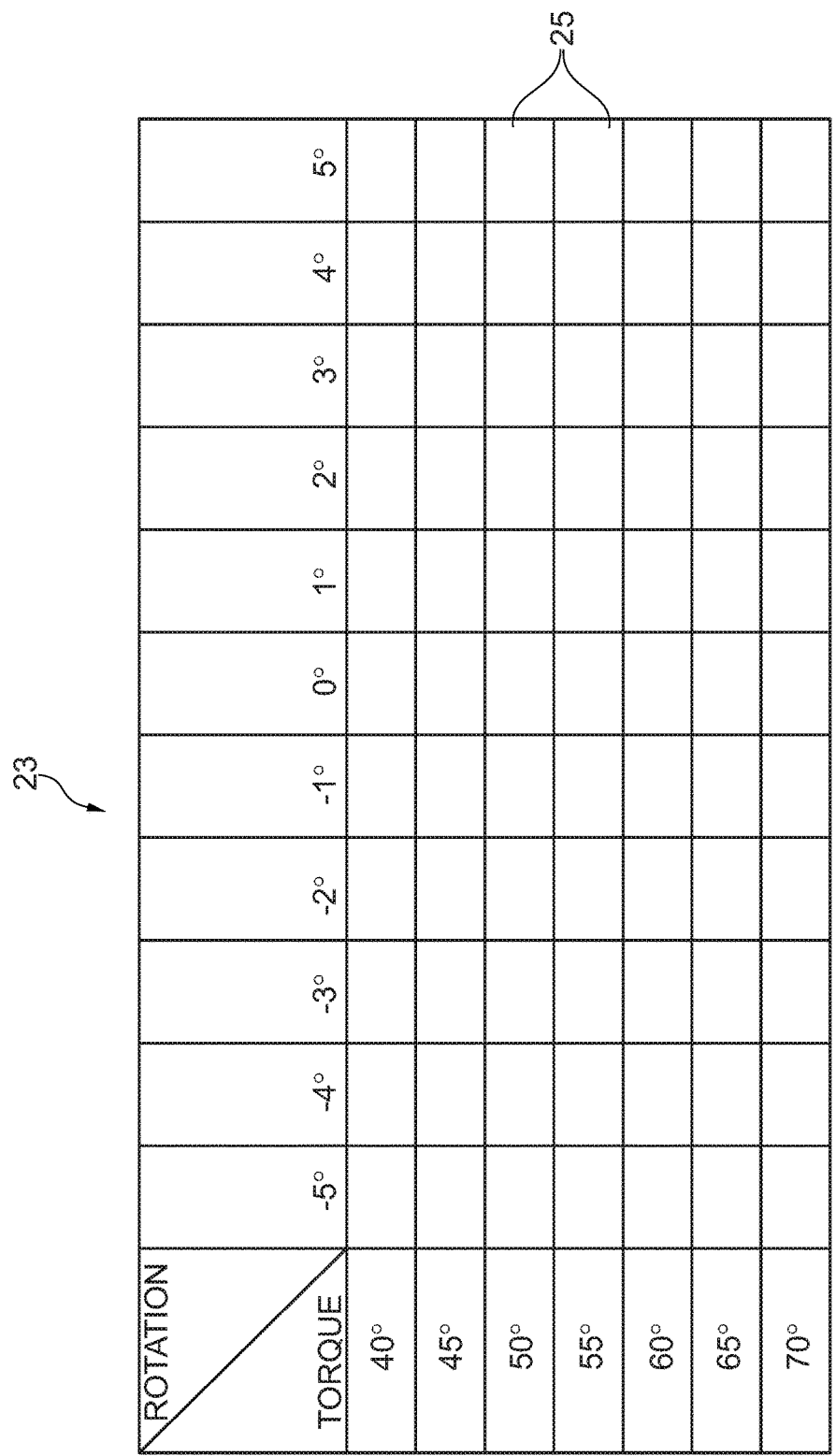

FIGS. 6A-6D show several views of a raw bracket body for the tooth 1 of the upper jaw (UJ 1st), FIGS. 6E-6H show several views of a bracket body, produced from the raw bracket body of FIGS. 6A-6D, FIGS. 7A-7D show several views of a raw bracket body for the UJ or LJ 6th (tooth 6 of the upper jaw or lower jaw), FIGS. 8A-8D shown several views of a raw bracket body for the UJ or LJ 7th, FIGS. 8E-H show several views of a bracket body, produced from the raw bracket body of FIG. 8, FIG. 9 shows a perspective view of a target set-up, wherein a raw pad is arranged on a tooth and a gap between both is filled with plastic, FIGS. 10A and 10B show a perspective view of a tooth, on which a finished bracket is introduced, FIG. 11 is a top view on a raw pad library and FIG. 12 is a top view on a bracket body library.

First of all, there are provided a band of material for pads (100 m long, 5 cm wide and 0.4 mm thick) made of stainless steel as well as a punch with a punching stamp, to punch out raw pads out of the pad material band using the punch. The punch punches out several identical raw pads from an inlaid pad material section of the pad material band, wherein the buccal/lingual perimeter of the same is adapted to the tooth for which the raw pad is produced. Instead of a pad material band, it is alternately possible also to use a sheet of pad material.

FIGS. 1A-1D the six side views as well as a perspective view of a raw pad 5 for the tooth 21 are shown, which was produced that way. The raw pad 5 is flat and presents a constant material thickness over the whole area. The buccal/lingual perimeter 5U presents practically the form of a triangle which enables the raw pad 5 being adapted correctly to the tooth 21. The edges of the buccal/lingual perimeter 5U, which were generated when punching out, were eliminated in a subsequent compression step, which produces the rounded lateral surfaces of said perimeter 5U.

Analogically, FIGS. 2A-2D show a raw pad 5 produced according to the same method for the tooth 23, whereas said raw pad 5 differentiates itself from that of FIG. 1 exclusively through the other form of the buccal/lingual perimeter 5U.

FIGS. 3A-3G show the six side views as well as a perspective view of a raw pad 5 for the tooth 27. The raw pad 5 was produced following the same method, as described with reference to FIGS. 1 and 2, still two additional bending steps were however carried out. In a first bending step, a mesial 5*m* and a distal 5*d* wing section was formed by folding it over in a press with an appropriate bending tool. In a second bending step, an occlusal section 5*o* of the raw pad 5 was formed in a press with an appropriate bending tool. This occlusal section 5*o* rests occlusally on the tooth 27 in the status inserted in the patient.

FIGS. 4A-4G show the six side views as well as a perspective view of a raw pad 5 for the tooth 35. The raw pad 5 was produced following the same method, as described with reference to FIGS. 1 and 2, a mesial 5*m* and a distal 5*d* wing section was however formed in a further bending step.

FIGS. 5A-5G show the six side views as well as a perspective view of a raw pad 5 for the tooth 37. The raw pad 5 was produced following the same method, as described with reference to FIGS. 1 and 2, still two additional bending steps were however carried out, as described previously with reference to FIG. 3: In a first bending step, a mesial 5*m* and a distal 5*d* wing section was formed by folding it over in a press with an appropriate bending tool. In a second bending step, an occlusal section 5o of the raw pad 5 was formed in a press with an appropriate bending tool. This occlusal section 5o rests occlusally on the tooth 37 in the status inserted in the patient.

The raw pads 5 obtained that way were sorted into a raw pad library 19 which is represented on FIG. 11. The raw pad library 19 comprises 16 times 8 raw pad containers 21, which are arranged in a matrix pattern. In the row $UJ_{LT}$ and $LJ_{LT}$ are respectively 16 raw pad containers 21, that is to say that a raw pad container 21 is provided for every tooth of the upper jaw and of the lower jaw. The raw pad containers 21 are arranged analogically to the FDI dental notation in the dentistry: from the tooth 8 (8th) left starting over the 1st to the right up to the 8th of the other half of the face. Accordingly, the raw pad containers are designated as 18 via 11 and 21 to 28, respectively as 48 via 41 and 31 to 38. Raw pads 5 belonging to or being adapted to the respective tooth are situated in each of said raw pad containers 21.

The row $UJ_{LT}$ and $LJ_{LT}$ contains the raw pads 5 for the upper jaw respectively the lower jaw with large teeth. The row $UJ_{ST}$ and $LJ_{ST}$ contains the raw pads 5 for the upper jaw respectively the lower jaw with small teeth. The row $UJ_{OST}$ and $LJ_{OST}$ contains the raw pads 5 with occlusal sections 5o for the upper jaw respectively the lower jaw with small teeth, in this instance only for the teeth 17, 18, 28, 27 as well as 34, 35, 37, 38, 44, 45, 47 and 48. In the row $UJ_{WLT}$ and $LJ_{WLT}$ there are contained the raw pads 5 with wing sections 5m, 5d for the upper jaw respectively the lower jaw with large teeth, in this instance only for the teeth 14, 15, 16, 17, 18, 24, 25, 26, 27, 28 as well as 34, 35, 36, 37, 38, 44, 45, 46, 47 and 48.

To obtain now a patient-specific pad, the procedure is as follows: An impression of an upper jaw and lower jaw of a patient respectively is taken and a plaster model is prepared by using the former. The plaster models are mounted respectively arranged into an articulator which mirrors the relative position of the jaws relative to one another (malocclusion models). The target set-up is completed from said malocclusion model which depicts the planned situation at the end of the treatment. To prepare it, the teeth are cut out individually from the malocclusion models of the patient and then re-assembled in the target situation to reach, thereby producing the target set-up.

A suitable raw pad 5 respectively for the teeth to be treated is taken from the raw pad library 19. The taken raw pads 5 are further adapted onto the corresponding teeth of the plaster model (target set-up) possibly by hand, wherein consequently the form and/or the size can be adapted, but bendings can still be carried out manually. Subsequently, the raw pads 5 are respectively held on the corresponding tooth in the target set-up and a gap 27 between the tooth and the raw pad 5 is filled with a filling material made of plastic, as shown in FIG. 9. In this manner, the raw pad 5 is given a patient-specific glued surface 3K and thus becomes a pad 3. This patient-specific glued surface 3K is in positive engagement with the tooth surface and can later be laid onto the tooth of the patient in a form locking manner and then be fixedly connected thereto using a glue.

The patient-specific pads 3 obtained that way are subsequently connected respectively to a patient-specific bracket body 7 which is taken from a bracket body library 23 which library is built analogically to the raw pad library, described as follows.

FIGS. 6A-6D show different views of a raw bracket body 9 for an UJ 1st, wherein said presents a fixing section 9f, a spacer section 9d, a slot 11, a hook 13 and a wing 15. FIGS. 6E-6H show the cut surface 10, which is arranged according to the three parameters.

FIGS. 7A-7D show different views of a raw bracket body 9 for an upper jaw (UJ) or a lower jaw (LJ) tooth 6 (6th), wherein said presents a fixing section 9f, a spacer section 9d, a slot 11, two hooks 13 and two wings 15.

FIGS. 8A-8D show different views of a raw bracket body 9 in the form of a little tube 17 for an upper jaw (UJ) or a lower jaw (LJ) tooth 7 (7th), wherein said also presents a spacer section 9d.

The raw bracket bodies 9 were produced in a metal injection moulding (MIM) process (alternately in a selective laser melting process) and consist of a cobalt-chrome alloy (alternately for instance made of stainless steel). The hooks 13 and wings 15 respectively present a material tapering on their end facing the slot 11, so that they can be bent respectively manually into a suitable angular position around the slot 11.

To make an optimal slot 11 available for the treatment the raw bracket bodies 9 of the FIGS. 6 and 7 are fastened to a carrier with their fixing sections 9f. Approx. 100 pieces can be fixed to the carrier. The carrier with the raw bracket bodies 9 is dipped into a suitable liquid bath in which the slot 11 of every single raw bracket body 9 is trimmed by means of a wire erosion procedure. This operation may also involve several passes (for planing). The result is a very precise slot 11 with a minimal margin of error with respect to the norm.

The raw bracket body of FIG. 8 has no fixing section, because it has no slot which must be produced extremely precisely for the treatment.

After this step, the raw bracket bodies 9 of the FIGS. 6 to 8 are fixed with their slot side end in a corresponding negative form (to this end), whereas alternately a fastening is possible on the opposite end. The spacer section 9d of the respective raw bracket bodies 9 is cut through with various angles using a saw. Three parameters can be set during the cutting-through phase:

The first parameter is a distance of the resulting cut surface of the spacer section 11. The smaller this distance can be selected, the less a patient can feel the bracket.

The second parameter is an angle about the longitudinal axis of the slot 11 (mesio-distal axis). According to the deviation of the cutting angle from an average default value, the torque applied is more or less important, see FIG. 6 for nomenclature.

The third parameter is an angle with respect to a vertical line towards the longitudinal axis of the raw bracket body 9 (occlusal-gingival axis). According to the deviation of the cutting angle from an average default value, the rotation applied is more or less important, see FIG. 6 for nomenclature.

For a raw bracket body 9, these three parameters are now established and the spacer section 9d is cut through accordingly with a saw, whereby a bracket body 7 is produced. FIGS. 6E-6H show the raw bracket body 9 of FIGS. 6A-6D, at which the spacer section in terms of torque at 55° and in terms of rotation at 15° was cut through, whereby the bracket body 7 of FIGS. 6E-6H is produced. FIGS. 8E-8H show the raw bracket body 9 of FIGS. 8A-8D, at which the spacer section in terms of torque at 20° and in terms of rotation at 15°, respectively, was cut through. FIGS. 8E-8H show the cut surface 10 arranged corresponding to these three parameters.

The bracket bodies 7 obtained in this manner are sorted into bracket body containers 25 of a bracket body library 23 (FIG. 12), wherein respectively a bracket body library is available for each raw bracket body 9 of the FIGS. 6 to 8. In other words, the raw bracket body 9 of FIG. 6 has its own bracket body library, just like that of FIGS. 7 and 8.

FIG. 12 shows a bracket body library 23, which is built analogically to the raw pad library and is filled with bracket bodies 7. The bracket bodies 7 are divided in 1° steps in terms of rotation of −5° to +5° and in terms of torque divided into 5° steps from 40° to 70°. Naturally, other interval limits as well as other interval steps can here be used in particular also depending on the raw bracket body 9, i.e. for the raw bracket body 9 of FIG. 6 other interval limits and other interval steps can be used as for that of FIG. 7. The bracket bodies 7 along with the pad 3 form a finished bracket 1.

The method of production of a patient-specific bracket continues as follows: A patient-specific pad 3 is already fixed to the teeth in the set-up to be treated. For every pad 3, a suitable bracket body 7 is now taken from the bracket body library 23 and glued fixedly to its respective pad 3. The bracket bodies 7 are advantageously guided to the respective pad 3 via a "mechanical finger" and then glued fixedly thereto.

A 2D-scan of the UJ model and/or U model is taken from the bracket set-up obtained that manner from the corresponding cranial respectively caudal direction (elevation view), so as to bend a corresponding archwire using a wire bending machine using these data.

Subsequently, the plaster models are soaked in a water bath which enables to release the pads with the bracket bodies fixedly glued thereto, which then are welded fixedly to one another using a laser.

The brackets 1 produced in that manner are placed on a plaster model of the patient (malocclusion model), see FIGS. 10A and 10B, and there fixed, to produce a transfer tray, for example made of silicone.

A raw pad 5 was represented respectively in FIGS. 1 to 5 for the teeth 21, 23, 27, 35 and 37. It is generally possible, to develop for every tooth of the upper and/or lower jaw respectively a raw pad 5 adapted especially to this tooth. Alternately, it is possible to use a raw pad 5 for several teeth, for instance a raw pad 5 for the teeth 32, 31, 41 and 42.

The raw pad library 19 according to FIG. 11 in each row comprises 16 raw pad containers 21, in which raw pads 5 are arranged respectively for a tooth. Consequently, raw pads 5 are respectively provided from the tooth 8 (8th) of the one side to the 8th of the other side. The raw pad library 19 in an alternative embodiment in each row comprises 14 raw pad containers 21 in which raw pads 5 are respectively arranged for a tooth (from the 7th to the 7th). Consequently, raw pads 5 are respectively provided from the 7th of the one side to the 7th of the other side.

In the context of the present invention, by matrix-like arrangement is meant an arrangement in lines and columns.

The bracket body library 23 comprises bracket body containers 25 with bracket bodies 7 arranged therein. The bracket body containers 25 respectively the bracket bodies 7 arranged therein are hence sorted per parameter values of the three parameters (distance between cut surface and slot, angle of mesial-distal axis, angle of occlusal-gingival axis). It is generally possible to vary all three parameters in a bracket body library 23 of a bracket body 9. It is hence for instance possible again to produce the bracket body library 23 of FIG. 12 with the same values for torque and rotation, whereas however the third parameter (the distance between cut surface and slot) is varied, for instance enlarged or reduced by 1 mm. That way, there would be twice the bracket body library 23 of FIG. 12: once with a larger distance and once with a smaller distance, through which a new bracket body library 23 is built. The matrix-like arrangement of FIG. 12 is hence extended into the third dimension, in which the additional parameter is varied. This general version is in practice as a rule not necessary: Since the distance between cut surface and slot should always be as small as possible so that the generated bracket 1 disturbs the patients as little as possible, the bracket body library 23 of FIG. 12 can be sufficient, with which the distance between cut surface and slot is as small as possible.

An advantageous method for producing a patient-specific bracket having a patient-specific pad and a patient-specific bracket body can therefore be subdivided into the following steps:

1. Production of a raw pad library:
    Providing a preferably flat section of pad material,
    Providing a punch with at least one punching stamp for punching out tooth-specific raw pads out of the section of pad material,
    Punching out the tooth-specific raw pads out of the section of pad material using the punch,
    optional pre-assembly of the raw pads.
2. Production of a bracket body library:
    Providing raw bracket bodies having a spacer section,
    optionally producing highly precise slots in the raw bracket bodies (for instance by wire erosion),
    Cutting of the spacer sections with selected parameter values for the three parameters
3. Generating a patient-specific target set-up, in particular made of plaster, of the upper jaw and/or lower to be treated of a patient.
4. Selecting a raw pad from the raw pad library for a tooth to be treated of the patient.
5. Filling a gap between the raw pad and the corresponding tooth in the target set-up with a filling material, in particular made of plastic, to obtain a tooth-specific glued surface for the pad, which enables a positive locking with the clinical tooth of the patient.
6. Selecting a bracket body from the bracket body library for each pad.
7. Fixing the bracket body on the pad, to build the patient-specific bracket.

The method steps need not however be carried out in that order. It is hence for instance possible, alternatively to first connect the raw pads 5 with their corresponding bracket bodies 7 and to build the glued surface 3K only subsequently.

LIST OF REFERENCE NUMERALS

1 bracket
3 pad
3K glued surface of the pad
5 raw pad
5*m* mesial (wing) section of a raw pad
5*d* distal (wing) section of a raw pad
5*o* occlusal (wing) section of a raw pad
5U buccal/lingual perimeter
7 bracket body
9 raw bracket body
9*d* spacer section of the raw bracket body
9*f* fixing section of the raw bracket body
10 cut surface
11 slot
13 hook
15 wing
17 little tube
19 raw pad library 21 raw pad container
23 bracket body library
25 bracket body container
27 gap

The invention claimed is:

1. A method for producing at least one patient-specific modular bracket having a pad and a bracket body, comprising the steps of:
   providing a plurality of raw bracket bodies having a spacer section extending away from a slot and ending in a flat surface distal from the slot,
   customizing the raw bracket bodies to produce a plurality of different bracket bodies, wherein the step of customizing the raw bracket bodies to produce the plurality of different bracket bodies includes establishing a first parameter for cutting through the spacer section from the slot of the raw bracket body to set a height of the bracket body, establishing a second parameter for cutting through the spacer section at an angle to a mesio-distal axis of the raw bracket body to set a torque value of the bracket body, establishing a third parameter for cutting through the spacer section at an angle to an occlusal-gingival axis to set a rotation value of the bracket body, and cutting through the spacer section according to the first, second and third parameters to form a flat cut surface on the bracket bodies,
   providing at least one bracket body library formed of said bracket bodies,
   generating a patient-specific set-up, in particular made of plaster, of the teeth to be treated of an upper jaw and/or of a lower jaw of a patient,
   selecting a raw pad from a raw pad library for each of the patient's teeth to be treated,
   forming a patient-specific glued surface on each raw pad for producing the pad,
   selecting a bracket body from the bracket body library for each pad for respective connecting with the pad, and
   connecting one pad each to the flat cut surface of the corresponding bracket body thereby producing a patient-specific bracket for each of the patient's teeth to be treated.

2. The method according to claim 1 wherein the raw pads of the raw pad library are provided by
   providing a pad material section, which preferably is plane,
   providing a punch having at least one punching stamp for punching out at least one raw pad from the pad material section, and
   punching out of at least one raw pad from the pad material section by means of the punch.

3. The method according to claim 1, wherein the raw bracket bodies are produced by a MIM process or by a selective laser melting process.

4. The method according to claim 1, wherein the raw pads and/or the raw bracket bodies are produced from a biocompatible metal or a biocompatible alloy.

5. The method according to claim 1, wherein connecting each pad to its corresponding bracket body comprises gluing or welding.

6. The method according to claim 1, wherein the formation of a patient-specific glued surface on a raw pad comprises filling a gap between the raw pad and the corresponding tooth in the set-up using a filling material in order to allow for a form fit of the glued surface to the clinical tooth of the patient.

7. The method according to claim 1, wherein at least two of the three parameters are each varied in a selected interval limit with selected interval steps in order to generate the bracket body library, such that the bracket bodies are arranged with their respective differing parameter values.

8. The method according to one claim 1, comprising pre-assembling raw pads for specific teeth to provide the raw pad library.

9. The method according to claim 8, wherein the pre-assembling comprises an adaptation of the buccal/lingual perimeter of at least one raw pad to adapt this perimeter of the at least one raw pad to a certain tooth size or tooth form.

10. The method according to claim 8 wherein the pre-assembling includes a bending of selected sections of a raw pad to build mesial and/or distal wing sections of the raw pad which encompass the corresponding tooth at least by sections.

11. The method according to claim 8 wherein the pre-assembling includes a bending of an occlusal section of a raw pad, which section then rests occlusally on the corresponding tooth.

12. The method according to claim 8, wherein the pre-assembling includes the formation of lingual/buccal protrusions on the at least one raw pad to adapt it to a lingual concave/convex structure of a certain tooth.

13. The method according to claim 8, wherein a manual adaptation of the at least raw pad to its corresponding tooth is made, wherein said adaptation includes an adaptation of the form and/or of the size of the raw pad.

14. The method according to claim 1, wherein at least two different bracket bodies are provided, each being adapted to a certain tooth from 1st to 8th.

15. The method according to claim 1, wherein the brackets are respectively positioned in a malocclusion model of the patient on the matching tooth to be treated and a transfer tray is then obtained, in which the brackets are arranged in their relative position and orientation corresponding to the malocclusion.

16. The method according to claim 4, wherein the biocompatible metal or a biocompatible alloy comprises gold, silver or stainless steel or a cobalt-chrome alloy.

17. The method according to claim 8, wherein the pre-assembling comprises compression followed by stamping out.

* * * * *